(12) United States Patent
Zhang et al.

(10) Patent No.: US 9,353,345 B2
(45) Date of Patent: May 31, 2016

(54) SECURING APPARATUS AND METHOD

(71) Applicant: TA INSTRUMENTS-WATERS L.L.C., Milford, MA (US)

(72) Inventors: Guangtian Zhang, Medina, MN (US); Troy D. Nickel, Minneapolis, MN (US); Eugene Joseph Rausch, Buffalo, MN (US); Aaron M. Owens, Plymouth, MN (US)

(73) Assignee: TA INSTRUMENTS-WATERS L.L.C., Milford, MA (US)

( * ) Notice: Subject to any disclaimer, the term of this patent is extended or adjusted under 35 U.S.C. 154(b) by 160 days.

(21) Appl. No.: 13/940,948

(22) Filed: Jul. 12, 2013

(65) Prior Publication Data

US 2015/0017719 A1 Jan. 15, 2015

(51) Int. Cl.
*C12M 1/00* (2006.01)
*C12M 1/42* (2006.01)
*C12M 3/00* (2006.01)

(52) U.S. Cl.
CPC ............... *C12M 35/04* (2013.01); *C12M 21/08* (2013.01); *C12N 2527/00* (2013.01)

(58) Field of Classification Search
CPC ..... C12M 21/08; C12M 35/04; C12N 2527/00
USPC ........................................ 435/289.1; 269/266
See application file for complete search history.

(56) References Cited

U.S. PATENT DOCUMENTS

| | | | |
|---|---|---|---|
| 4,940,853 A * | 7/1990 | Vandenburgh | 435/395 |
| 7,513,546 B2 * | 4/2009 | Vranish | 269/266 |
| 2009/0019950 A1 | 1/2009 | Dingmann et al. | |
| 2010/0164160 A1 * | 7/2010 | Stevenson et al. | 269/266 |
| 2011/0291342 A1 * | 12/2011 | Gindy et al. | 269/266 |
| 2013/0160577 A1 | 6/2013 | Williams et al. | |

FOREIGN PATENT DOCUMENTS

| | | |
|---|---|---|
| AU | 2013205387 A1 | 5/2013 |
| WO | 0168800 A1 | 9/2001 |
| WO | 2012076636 A1 | 6/2012 |

OTHER PUBLICATIONS

Invitation to Pay Additional Fees dated Dec. 4, 2014 for International application No. PCT/US2014/045557.

(Continued)

*Primary Examiner* — Nathan Bowers
*Assistant Examiner* — Timothy Barlow
(74) *Attorney, Agent, or Firm* — McCarter & English, LLP; Deborah M. Vernon

(57) ABSTRACT

A securing apparatus includes a housing, a cam member, and a movable device that can be moved in a first direction to engage a first surface of the cam member to cause the cam member to move from a first position to a second position. When the cam member is in the first position, first and second movable members can be moved relative to the housing. When the cam member is in the second position, second and third surfaces of the cam member press respectively against the first and second movable members to trap the first and second movable members respectively between the second and third surfaces of the cam member and the housing such that the first and second movable members are fixed relative to the housing.

8 Claims, 7 Drawing Sheets

(56) References Cited

OTHER PUBLICATIONS

Mohammad Sotoudeh et al: "A Strain Device Imposing Dynamic and Uniform Equi-Biaxial Strain to Cultured Cells", Annals of Biomedical Engineering, vol. 26, No. 2, Mar. 1, 1998, pp. 181-189, XP55153356, ISSN: 0090-6964, DOI: 10.1114/1.88, p. 182 col. 1 li. 29-33, p. 182 col. 2 li. 32-p. 184 col. 1 li. 1; figures 1-2.
Daniel A. Shimko et al: 'A Device for Long Term, In Vitro Loading of Three-Dimensional Natural and Engineered Tissues', Annals of Biomedical Engineering, vol. 31, No. 11, Dec. 1, 2003, pp. 1347-1356, XP55153370, ISSN: 0090-6964, DOI: 10.1114/1.1626117 p. 1348 col. 2, 2nd; figures 1-2.
International Search Report and Written Opinion dated Mar. 19, 2015 for International application No. PCT/US2014/045557.
Biomechanical signals and the C-type natriuretic peptide counteract catabolic activities induced by IL-1? in chrondrocyte/agarose constructs, Ramachandran et al. Arthritis Research & Therapy 2011, 13:R145, http://arthritis-research.com/content/13/5/R145.

\* cited by examiner

SECURING APPARATUS AND METHOD

BACKGROUND

This disclosure relates to an apparatus for securing a movable member.

Tissue engineering researchers aim to grow and organize cells in a laboratory setting by mimicking the body's environment. This process, referred to as cell culture, includes supplying cells with a nutrient-rich fluid and a support structure inside of a temperature and humidity-controlled setting. The support structure may consist of a matrix that is found in tissues of the body, or it may consist of a fabricated biocompatible material, referred to as a scaffold. When samples of a tissue explant or tissue engineering construct (containing living cells) are being cultured, it is often advantageous to physically stimulate the biological material by applying an external force or loading that replicates the cellular mechanical environment of the body.

This physical stimulation of the samples can be accomplished, for example, by using a movable member to apply strain to the construct. A device that is capable of stimulating multiple samples in order to make comparison is desirable to accelerate the research effort. Positioning multiple movable members relative to their corresponding samples prior to commencement of the physical stimulation can be challenging. For example, if the movable members are released accidentally, the members can crash into the samples and potentially cause damage to the samples. It can be difficult to properly position all of the movable members relative to their respective samples prior to commencement of the physical stimulation.

SUMMARY

All examples and features mentioned below can be combined in any technically possible way."

In one aspect, a securing apparatus includes a housing, a cam member, and a movable device that can be moved in a first direction to engage a first surface of the cam member to cause the cam member to move from a first position to a second position. When the cam member is in the first position a first movable member can be moved relative to the housing. When the cam member is in the second position a second surface of the cam member presses against the first movable member to trap the first movable member between the second surface of the cam member and the housing such that the first movable member is fixed relative to the housing. When the cam member is in the first position a second movable member can be moved relative to the housing. When the cam member is in the second position a third surface of the cam member presses against the second movable member to trap the second movable member between the third surface of the cam member and the housing such that the second movable member is fixed relative to the housing.

Embodiments may include one of the following features, or any combination thereof. The movable device is a screw. The movable device can be moved in a second direction which allows the cam member to move from the second position towards the first position. The first and second movable members are each shafts which can be used to physically stimulate a respective sample which includes one or more of a tissue explant or tissue engineering construct. The securing apparatus can further include a friction member which is positioned in a friction fit about the first movable member. The friction member is positionable along a longest dimension of the first movable member and engageable with a portion of the housing in order to hold the first movable member in a fixed position against a force of gravity. The securing apparatus can further include a rolling member which is interposed between the cam member and the movable device to increase a clamp force when the cam member is in the second position. The first and second movable members are each shafts which can be used to physically load a respective sample. The first and second movable members are each shafts which can be used to physically load respective samples that have varying dimensions.

In another aspect, a method of positioning a plurality of movable members includes providing each movable member with a friction member which is positioned in a friction fit about the movable member. Each movable member is moved relative to a housing such that its respective friction member is engaged against a respective one or more portions of the housing to position the friction member along a longest dimension of its respective movable member. Gravity is allowed to force each friction member against one of the portions of the housing to suspend each movable member at a desired position. One or more of the movable members can be suspended in a position to provide physical stimulation to a sample. One or more of the movable members can be suspended in a position to not provide physical stimulation to a sample.

Embodiments may include one of the above and/or below features, or any combination thereof. The housing is lowered in a controlled manner such that one or more of the movable members comes into contact with a respective sample, thereby avoiding damage to one or more of the samples. The lowering step causes each friction member of these one or more movable members to become disengaged from its respective portion of the housing such that a weight of each of these one or more movable members and their respective friction members pre-load a respective sample. The respective one or more portions of the housing against which a respective friction member can be forced partially define a cavity within which a respective friction member can be moved when that friction member's movable member is moved. Each movable member and its respective friction member can be moved with substantially no resistance from friction when the friction member is not in contact with one of the portions of the housing. Each cavity allows pre-loading of a respective sample with only the weight of a respective shaft and friction member. The movable members are secured against movement relative to the housing. Each friction member is an O-ring.

In another aspect, a securing apparatus includes a housing; a cam member, a motor, and a movable device that can be moved in a first direction to engage a first surface of the cam member to cause the cam member to move from a first position to a second position. When the cam member is in the first position a first movable member can be moved relative to the housing. When the cam member is in the second position a second surface of the cam member presses against the first movable member to trap the first movable member between the second surface of the cam member and the housing such that the first movable member is fixed relative to the housing. The motor is operable when the cam member is in the second position to move the housing and the first movable member such that the first movable member can physically stimulate a sample.

Embodiments may include one of the above and/or below features, or any combination thereof. An O-ring is included which is positioned in a friction fit about the first movable member, the O-ring being positionable along a longest dimension of the first movable member and engageable with a portion of the housing in order to hold the first movable member in a fixed position against a force of gravity. A rolling member is included which is interposed between the cam member and the movable device to increase a clamp force when the cam member is in the second position.

DETAILED DESCRIPTION

The description below discloses a securing apparatus which can be used to apply physical stimulation to one or more samples (e.g. tissue explant or tissue engineering constructs). This apparatus enables a multiplicity of movable members to be accurately positioned relative to their respective samples. The movable members can then be secured in place so that a controlled amount of physical stimulation can be applied to each sample.

Figure 1:
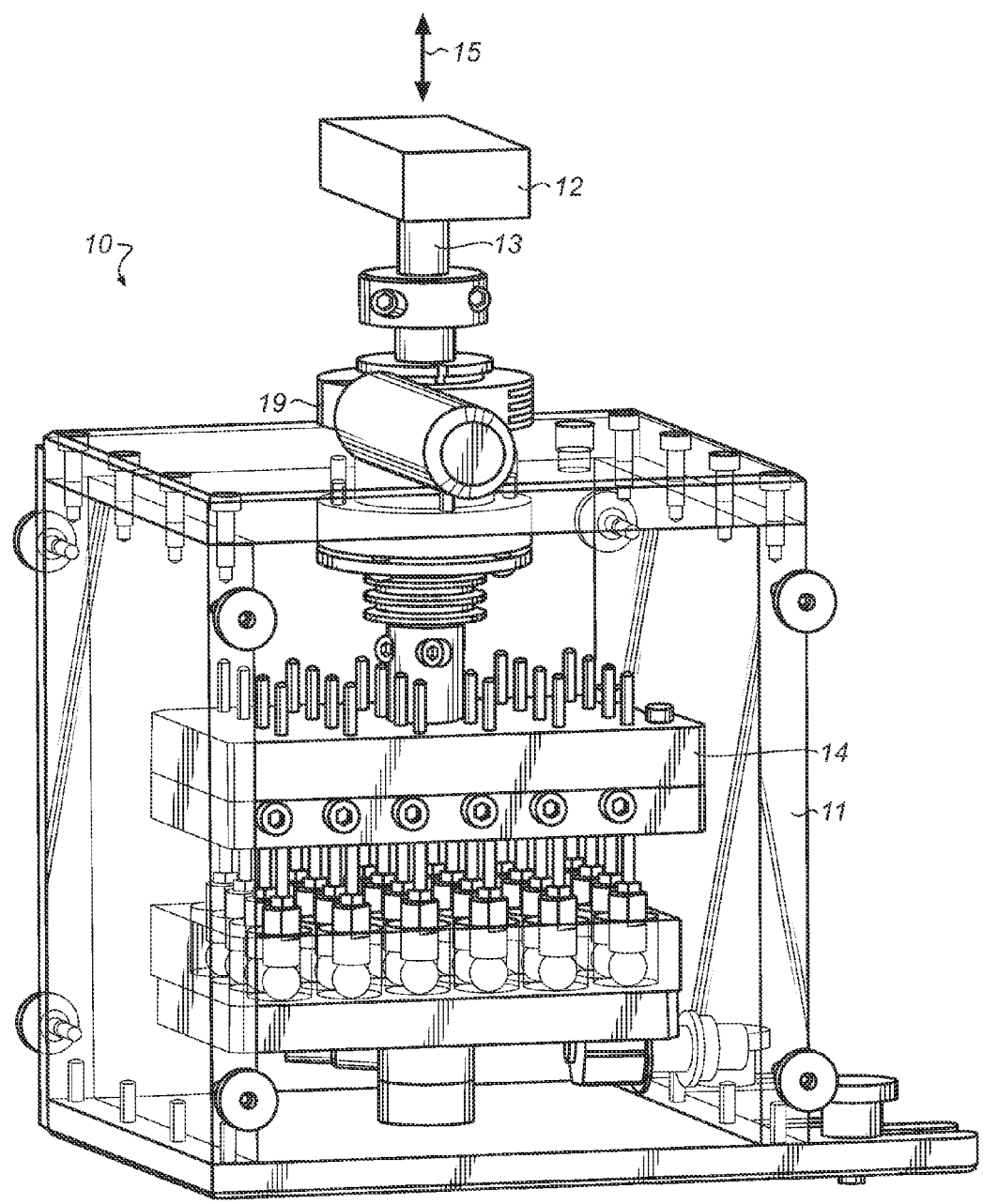
FIG. 1 is a schematic perspective view of an apparatus used to apply physical stimulation to tissue engineering construct samples.

With reference to FIG. 1, an apparatus 10 is shown which includes a transparent chamber 11. A front wall of the chamber 11 has been removed to facilitate viewing. A motor 12 is connected to a shaft 13. Within the chamber 11 is located a housing 14 which is rigidly secured to the shaft 13. The motor 12 can move the shaft 13 and thus the housing 14 back and forth along a double-headed arrow 15. A clamp 19 is used to lock the shaft 13 in position relative to the chamber 11 during setup of the housing in a sterile environment prior to the shaft 13 being connected to the motor 12 (explained further below).

Figure 2:
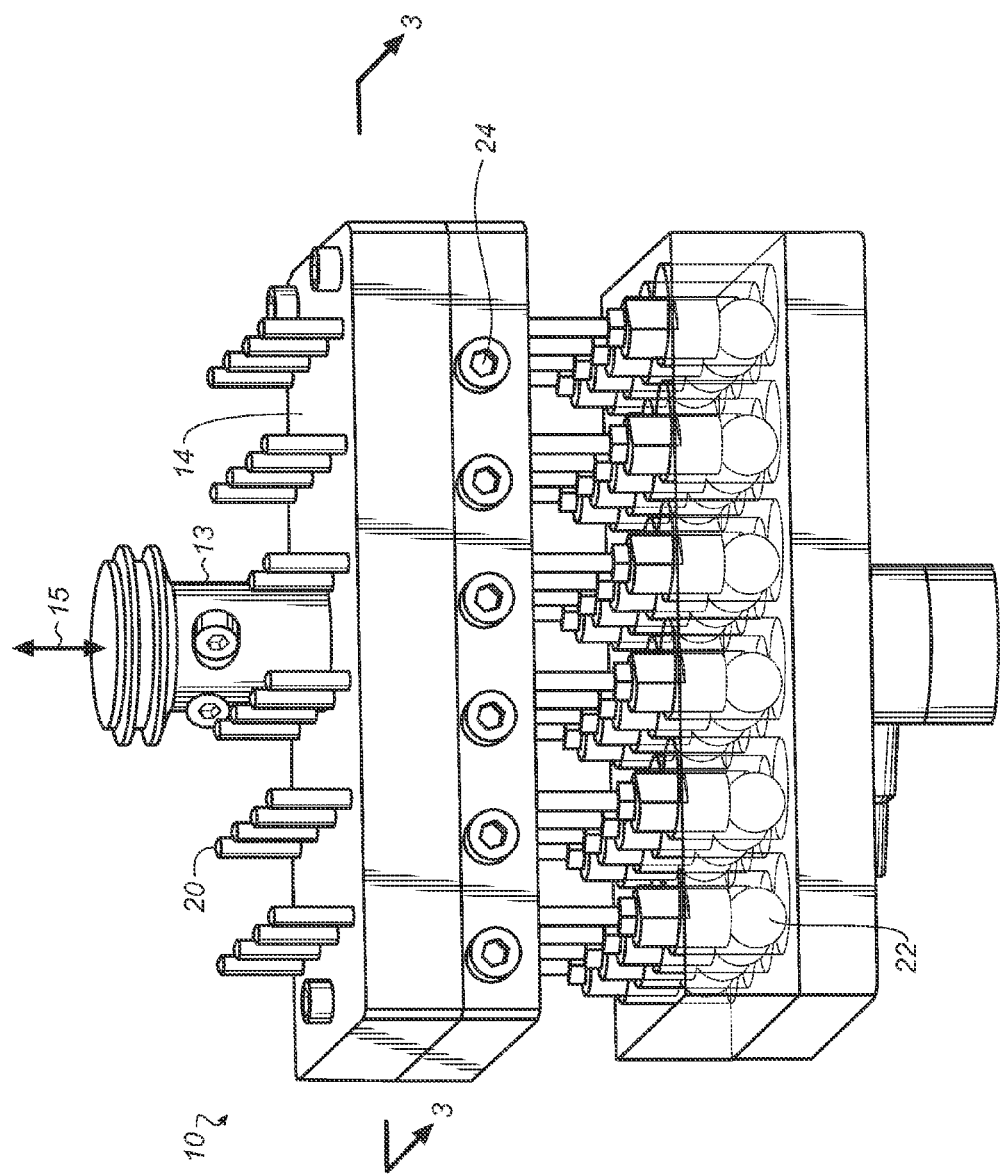
FIG. 2 is a schematic perspective view of a portion of the apparatus of FIG. 1.

In FIG. 2 a multiplicity of twenty-four movable members in the form of shafts 20 each pass through respective orifices in the housing 14. Of course a different number of shafts can be used. When the shafts 20 are fixed in position relative to the housing 14 (explained further below), and the housing is moved back and forth in the direction of the arrow 15 by the motor 12 (FIG. 1), the shafts 20 can each transmit a physical stimulation in the form of a strain to a respective sample 22 (e.g. tissue explant or tissue engineering constructs). A series of twelve movable devices in the form of set screws 24 (six are hidden from view on the back side of the housing 14) are each used to secure two of the shafts 20 in place relative to the housing 14 (explained further below).

Figure 3:
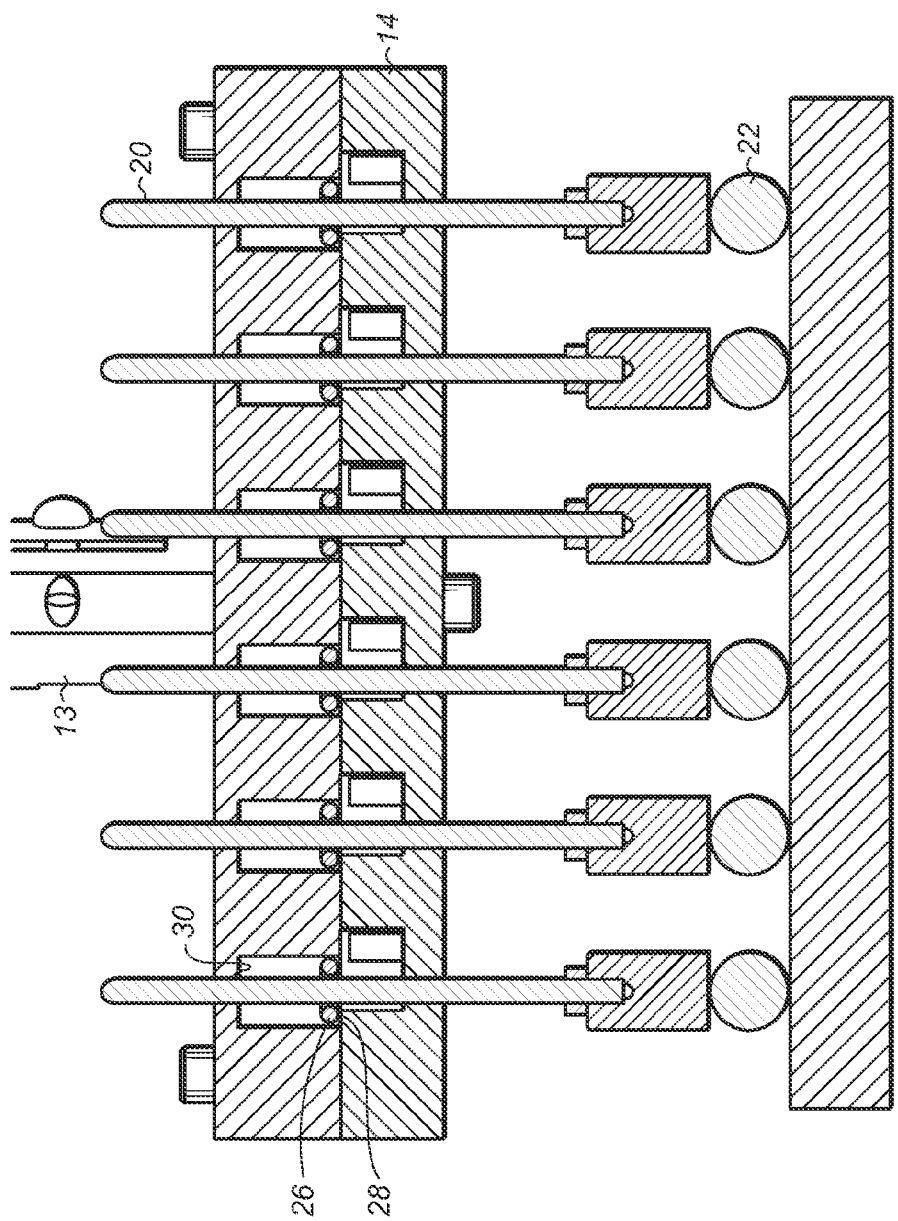
FIG. 3 is a partial sectional view of FIG. 2 taken along lines 3-3.

Turning to FIG. 3, the housing 14 is shown along with six of the shafts 20 and the samples 22. Each shaft 20 has an O-ring 26 (i.e. a friction member) which is positioned in a friction fit about the shaft 20. The O-ring 26 is positionable along a longest dimension of the shaft 20 and engageable with a portion of the housing 14 in the form of a lower lip 28 in order to hold the shaft 20 in a fixed position against a force of gravity when the shaft 20 is free to move in a direction parallel with the shaft's longest dimension (explained further below). In other words, gravity is allowed to force each O-ring against a respective lower lip 28 to suspend each shaft at a desired position. When the shaft 20 is free to move, an operator can grasp a top portion of the shaft and move the shaft by pulling the shaft up until the O-ring 26 engages another portion of the housing 14 in the form of an upper lip 30. If the operator then continues to pull the shaft 20 up, the O-ring 26 will be repositioned to be relatively lower on a longest dimension of the shaft. The lower and upper lips 28 and 30 partially define a cavity 29. The cavity 29 is wider and longer than the O-ring 26. As such each shaft 20 and its respective O-ring can be moved with substantially no resistance from friction when the O-ring is not in contact with one of the lips 28 and 30.

When the operator releases the shaft 20, gravity will pull the shaft down until the O-ring 26 contacts the lower lip 28 (assuming there is no sample 22 that prevents the O-ring 26 from contacting the lip 29). Likewise, when the shaft 20 is free to move, an operator can grasp a top portion of the shaft and push the shaft down. This causes the O-ring 26 to be forced against the lip 28 and to be repositioned to be relatively higher on the shaft. As such, each shaft 20 can be positioned relative to the housing 14. An advantage of using the O-rings 26 is that an operator can suspend the shafts 20 at different heights. This arrangement provides the freedom to choose active samples which receive physical stimulation from respective shafts and control samples which do not receive physical stimulation from any shafts.

It should be noted that the first portion of the physical stimulation setup takes place in a sterile environment in which the motor 12 is not present. As a first step the operator would manually pull all or some of the shafts 20 down so that they are in a lowered position (see the previous paragraph). This step can be performed automatically instead of manually if desired. A setup aid fixture can also be used to adjust the shafts at desired heights relative to the housing. Each of the samples is then positioned under a respective one of the shafts 20. The operator would then manually lower the housing 14 so that a bottom of one or more shafts comes into contact with its respective sample. The housing is manually lowered to the point where each of the O-rings has disengaged from (i.e. is hovering above) the lower lip 28 but has not come into contact with the upper lip 30. As such, the shafts 20 are positioned relative to the housing 14. Now the weight of each shaft and its respective O-ring pre-load its respective sample. The operator now secures the housing 14 to the main structure. Prior to commencement of the physical stimulation of the samples, the shafts 20 are secured so they do not move relative to the housing. This procedure is explained below.

Figure 4:
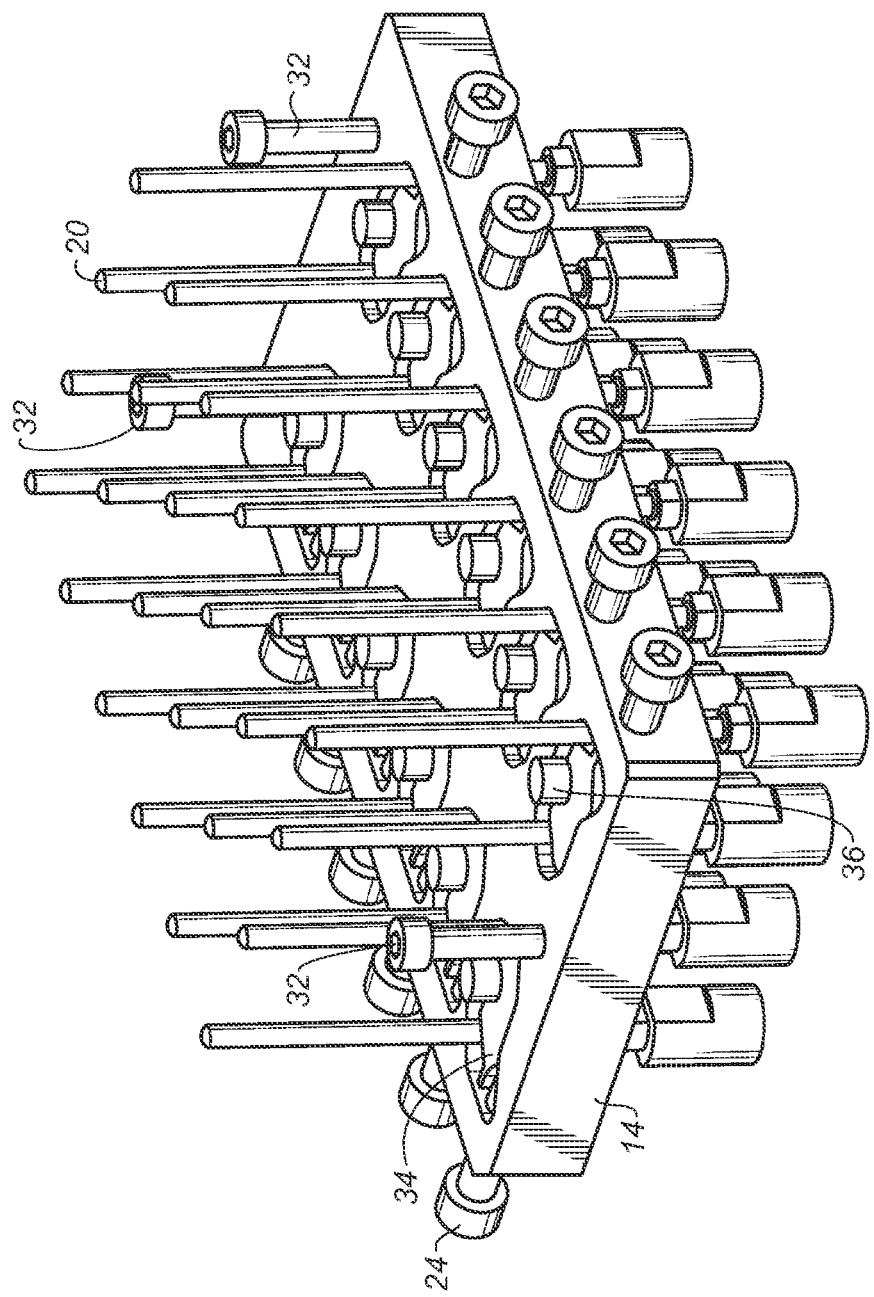
FIG. 4 is a schematic perspective view of a portion of the apparatus of FIG. 1.
Figure 5:
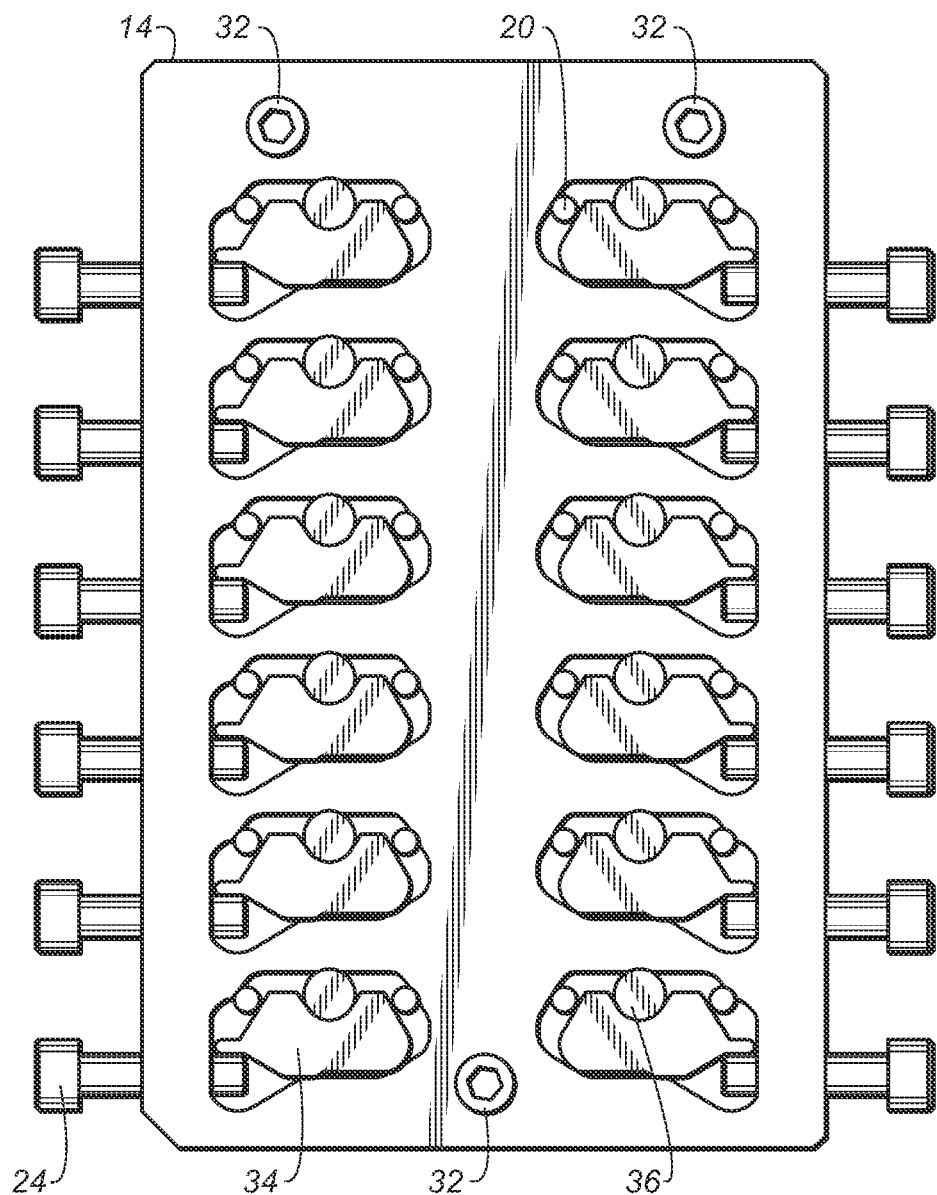
FIG. 5 is a top view of the portion of the securing apparatus shown in FIG. 4.

With reference to FIGS. 4 and 5, an upper portion of the housing 14 has been removed to facilitate viewing. A lower portion of the housing 14, the shafts 20 and the set screws 24 are all shown. A trio of securing screws 32 is used to secure the upper and lower portions of the housing 14 together. A respective cam member 34 is associated with each set screw 24 as well as a pair of the shafts 20. A respective polymer spring member 36 is associated with each of the cam members. The interactions of the shafts 20, set screws 24, cam members 34 and spring members 36 will be explained below.

Figure 6:
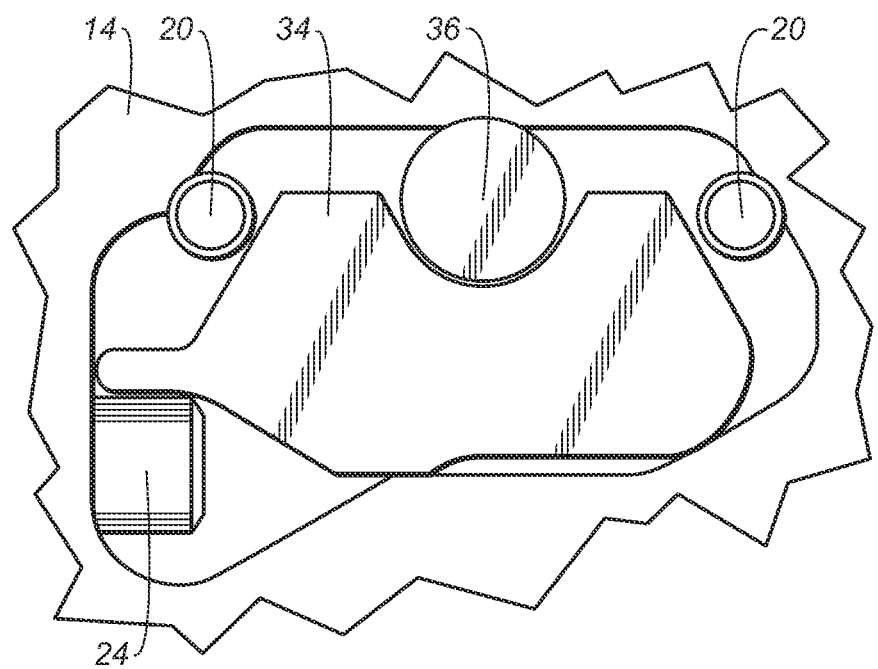
FIGS. 6 and 7 are magnified views of the same portion of FIG. 5 in different positions.
Figure 7:
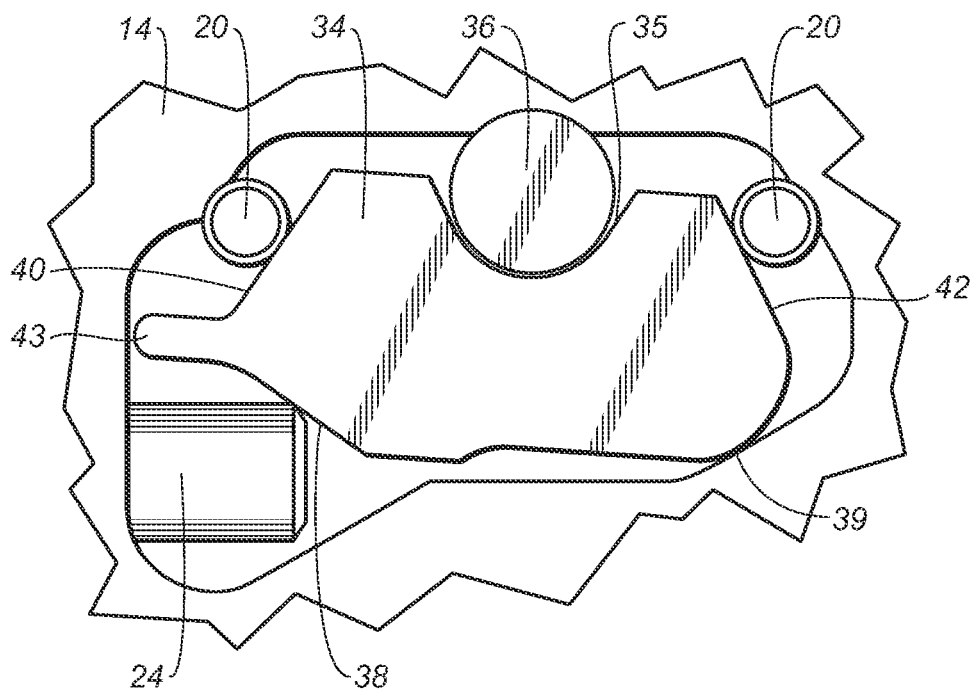

FIGS. 6 and 7 show a detail of one set of set screw 24, cam 34, and shafts 20, in two different positions. In FIG. 6, the set screw 24 is positioned further out of the housing 14 than in FIG. 7. In this position the cam member 34 is not engaging the two shafts 20 which have been positioned relative to the housing as described above. The operator then turns the set screw 24 which causes it to move further into the housing 14 as shown in FIG. 7. This movement causes the set screw 24 to engage a first surface 38 of the cam member 34 which causes the cam member to move from a first position shown in FIG.

6 to a second position shown in FIG. 7. At this position, the cam member transmits clamp load from set screw 24 to both shafts 20 in order to secure them to housing 14. The cam member 34 is rotated due to its interaction with the set screw 24, the shafts 20, the spring member 36 and the housing 14 at an angled surface 39.

When the cam member is in the first position, as shown in FIG. 6, the shafts 20 can each be moved relative to the housing 14 as discussed above regarding the O-rings. When the cam member 34 is in the second position, as shown in FIG. 7, second and third surfaces 40 and 42 of the cam member 34 press against the respective adjacent shafts 20 to trap the shafts between the respective second and third surfaces 40 and 42 of the cam member and the housing such that the shafts 20 are fixed relative to the housing. With the cam member 34 in the second position, the motor 12 is operated as described above to move the housing 14 and the shafts 20 to apply a physical stimulation (e.g. a strain) to the samples 22. Each of the set screws 24 for shafts 20 that will provide physical stimulation to samples is turned to lock its respective pair of shafts 20 in place relative to the housing 20 prior to commencement of the physical stimulation of the samples 22. Set screws 24 for those shafts 20 that will not provide physical stimulation to any of the samples 22 can optionally be left in the position shown in FIG. 7.

After the initial setup of the housing 14, samples 22, cam member 34, etc. as described above, the apparatus is removed from the sterile environment and the shaft 13 is connected to the motor 12. Displacement control is used to operate the motor 12 to move the housing 14. This displacement is determined based on the original geometry of the samples. It is preferable that all of the samples receive the same amount of physical stimulation. Preferably a mold is used to make all of the samples so that the samples are substantially the same size. However, there will likely be some sample-height variation which would require each shaft to be adjusted for its corresponding sample to obtain consistent pre-loads. As the shafts 20 preferably each have substantially the same weight, a pre-load applied by the gravity of the shafts 20, and optionally an added dead weight, before they are clamped provides a substantially equal initial strain to each of the samples. It is preferable for the preload on the samples to be only the weight of the shafts 20 and O-rings 26, so it's the same for all samples. As such, when the housing 14 is moved by a given displacement, all the samples should receive substantially the same amount of strain.

When the physical stimulation of the samples 22 is complete, the housing 14 and the shafts 20 are raised up from the samples. The samples can then be removed. The operator then turns each set screw 24 which causes it to move out of the housing 14, back to the position shown in FIG. 4. Each spring member 36 restores its respective cam member 34 to the position shown in FIG. 6 and away from the respective pair of shafts 20. The angled location 39 of the housing 14 and an arm 43 on the left side of the cam member 34 help to center the cam member 34 to ensure the cam does not apply any additional friction on the shafts 20. This allows the cam member 34 to move from the second position in FIG. 7 to the first position in FIG. 6, thereby releasing the shafts 20 to be moved as described above. The geometry on the housing 14 and cam member 34 are primarily provided in order to make sure that when the set screw 24 releases the cam member 34, the cam member 34 does not contact the shafts 20.

Figure 8:
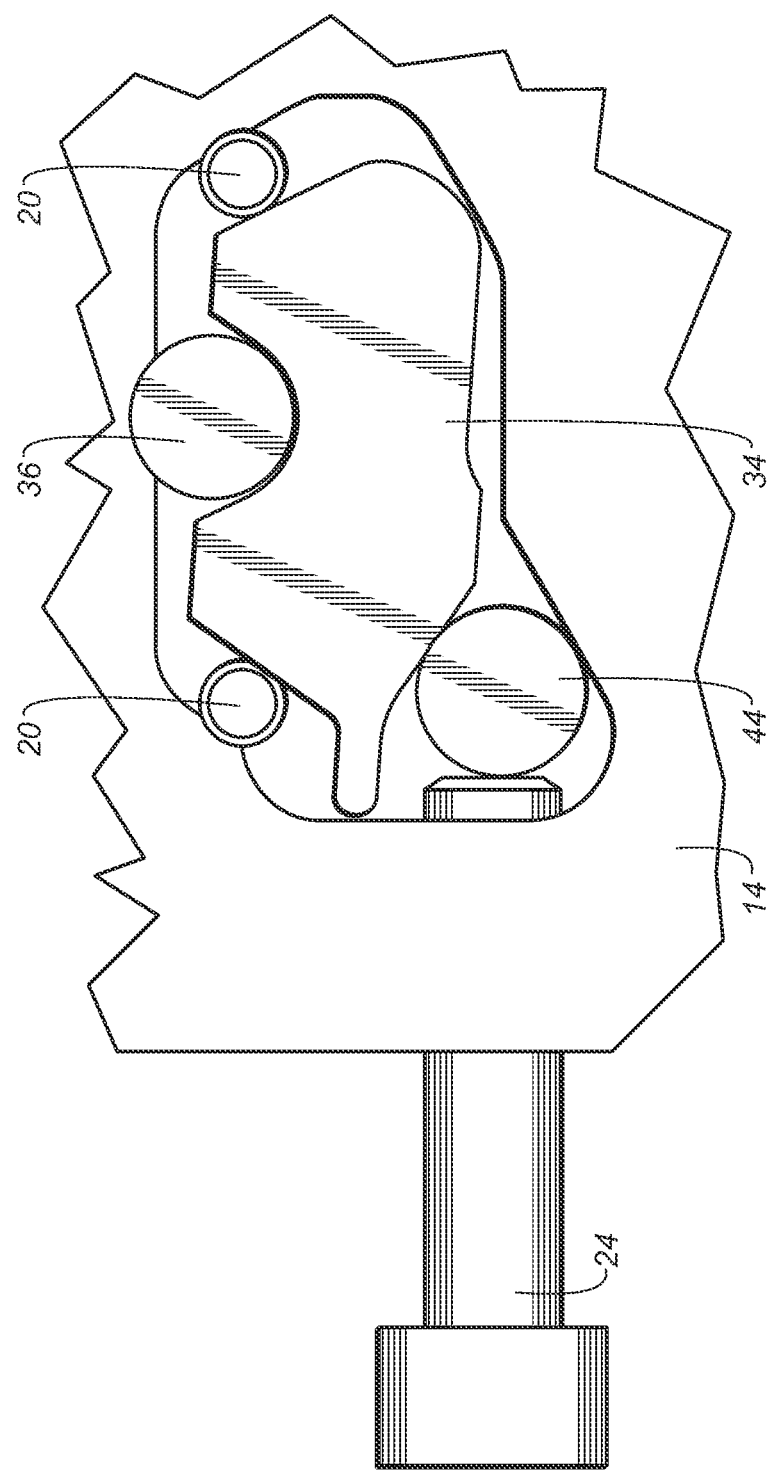
FIG. 8 is an alternative example of the arrangement shown in FIGS. 6 and 7.

Referring to FIG. 8, another example is shown which is similar to the example described with reference to FIGS. 6 and 7. In FIG. 8 a rolling member in the form of a cylinder or sphere 44 is interposed between the cam member 34 and the set screw 24 to increase a clamp force when the cam member 34 is in the second position (shown in FIG. 8).

A number of implementations have been described. Nevertheless, it will be understood that additional modifications may be made without departing from the scope of the inventive concepts described herein, and, accordingly, other embodiments are within the scope of the following claims.

What is claimed is:

1. A securing apparatus, comprising:
   a housing;
   a cam member;
   a spring member disposed between the cam member and the housing;
   a movable device that can be moved in a first direction to engage a first surface of the cam member to cause the cam member to move from a first position to a second position;
   a first movable member, wherein when the cam member is in the first position the first movable member can be moved relative to the housing, and wherein when the cam member is in the second position the cam member compresses the spring member and a second surface of the cam member presses against the first movable member to trap the first movable member between the second surface of the cam member and the housing such that the first movable member is fixed relative to the housing; and
   a second movable member located farther from the movable device than the first movable member, wherein when the cam member is in the first position the second movable member can be moved relative to the housing, and wherein when the cam member is in the second position the cam member compresses the spring member and a third surface of the cam member presses against the second movable member to trap the second movable member between the third surface of the cam member and the housing such that the second movable member is fixed relative to the housing.

2. The apparatus of claim 1, wherein the movable device is a screw.

3. The apparatus of claim 1, wherein the movable device can be moved in a second direction which allows the cam member to move from the second position towards the first position.

4. The apparatus of claim 1, wherein the first and second movable members are each shafts which can be used to physically stimulate a respective sample which includes one or more of a tissue explant or tissue engineering construct.

5. The apparatus of claim 1, further including a friction member which is positioned in a friction fit about the first movable member, the friction member being positionable along a longest dimension of the first movable member and engageable with a portion of the housing in order to hold the first movable member in a fixed position against a force of gravity.

6. The apparatus of claim 1, further including a rolling member which is interposed between the cam member and the movable device to increase a clamp force when the cam member is in the second position.

7. The apparatus of claim 1, wherein the first and second movable members are each shafts which can be used to physically load a respective sample.

8. The apparatus of claim 1, wherein the first and second movable members are each shafts which can be used to physically load respective samples that have varying dimensions.

* * * * *